United States Patent [19]

Brandley et al.

[11] Patent Number: 5,648,344
[45] Date of Patent: *Jul. 15, 1997

[54] METHODS OF TREATING INFLAMMATION USING SELECTION BINDING COMPOUNDS

[75] Inventors: Brian K. Brandley, Alameda; Michael Tiemeyer; Stuart J. Swiedler, both of Oakland; Margaret Moreland, Berkeley; Hans Schweingruber, Mountain View; Narasinga Rao, Alameda, all of Calif.

[73] Assignee: Glycomed Incorporated, San Diego, Calif.

[*] Notice: The term of this patent shall not extend beyond the expiration date of Pat. No. 5,428,025.

[21] Appl. No.: 922,328

[22] Filed: Jul. 30, 1992

Related U.S. Application Data

[63] Continuation-in-part of Ser. No. 683,458, Apr. 11, 1991, Pat. No. 5,211,937, which is a continuation-in-part of Ser. No. 637,868, Jan. 7, 1991, Pat. No. 5,143,712, which is a continuation-in-part of Ser. No. 613,113, Nov. 15, 1990, abandoned, which is a continuation-in-part of Ser. No. 559,836, Jul. 30, 1990, Pat. No. 5,211,936, and a continuation of PCT/US91/05416, Jul. 30, 1991.

[51] Int. Cl.$^6$ .................................................. A01N 43/04
[52] U.S. Cl. .................................. 514/61; 514/54; 514/62
[58] Field of Search .................................. 514/61, 54, 62; 536/119, 17.2

[56] References Cited

U.S. PATENT DOCUMENTS

| 4,563,445 | 1/1986 | Feizi et al. | 514/25 |
| 4,904,596 | 2/1990 | Hakomori | 435/240.27 |
| 5,030,723 | 7/1991 | Nudelman et al. | 536/53 |
| 5,217,870 | 6/1993 | Hession et al. | 435/7.24 |
| 5,324,663 | 6/1994 | Lowe | 435/320.1 |
| 5,428,025 | 6/1995 | Brandley et al. | 514/55 |

FOREIGN PATENT DOCUMENTS

WO90/13300  11/1990  WIPO ............ A61K 31/70

OTHER PUBLICATIONS

Brandley and Schnarr, *J. Leuk. Biol.*, 40:97–111 (1986).
Sharon and Lis, *Science*, 246:227–246, (1989).
Dodd and Jessel, *J. Neurosci.*, 5:3278–3294 (1985).
Regan et al., *Proc. Natl. Acad. Sci. USA*, 83:2248–2252 (1986).
Constantine-Paton et al., *Nature*, 324:459–462 (1986).
Tiemeyer et al., *J. Biol. Chem.*, 263:1671–1681 (1989).
Bevilacqua et al., *Proc. Natl. Acad. Sci. USA*, 84:9238–9242 (1987).
Fukuda et al., *J. Biol. Chem.*, 261:2376–2383 (1986).

Magnani et al., *J. Biol. Chem.*, 257:14365–14369 (1982).
Hakomori et al., *Biochem. Biophys. Res. Comm.*, 113:791–798 (1983).
Fukushi et al., *J. Exp. Med.*, 160:506–520 (1984).
Geng et al., *Nature*, 343:757–760 (1990).
Johnston et al., *Cell*, 56:1033–1044 (1989).
Geoffroy and Rosen, *J. Cell. Biol.*, 109:2463–2469 (1989).
Lasky et al., *Cell*, 58:1045–1055 (1989).
Bevilacqua et al., *Science*, 243:1160–1165 (1989).
Watson et al., *Nature*, 349:164–167 (1991).
Spertini et al., *Nature*, 349:691–694 (1991).
Finne et al., *J. Biol. Chem.* 264(10):5720–5735, 1989.
Fukushi et al., *J. Biol. Chem.* 259(16):10511–10517, 1984.
Hakomori et al., *J. Biol. Chem.* 259(Apr. 10):4672–4680, 1984.
Holmes et al., *J. Biol. Chem.* 260(12):7619–7627, 1985.
Kannagi et al., *Proc. Natl. Acad. Sci.* 79:3470–3474, 1982.
Levery et al., *Carb. Res.*, 178:121–144, 1988.
Nilsson, *Trends in Biotech.* 6:256–264, 1988.

*Primary Examiner*—John Kight
*Assistant Examiner*—Lara E. Chapman
*Attorney, Agent, or Firm*—Lyon & Lyon

[57] ABSTRACT

Ligands that bind to human selectin receptors are disclosed. The ligands are formulated with excipient carriers to form compositions which are administered to treated condition such as inflammation. The ligands have the structural formula III

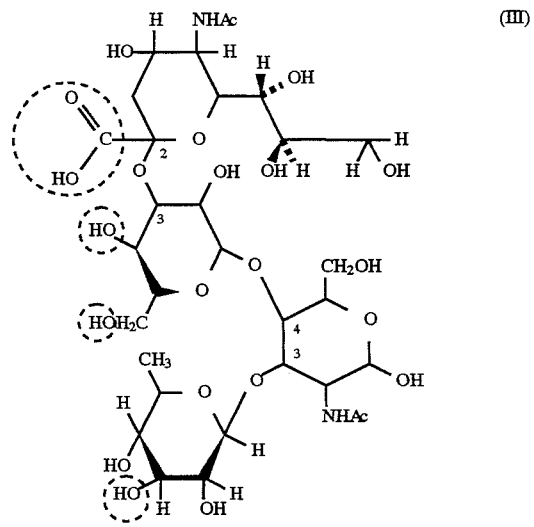

or molecules which have hydrogen bond donor groups equivalent to the circled groups with respect to their ability to form hydrogen bonds with a selectin under physiological conditions.

4 Claims, 6 Drawing Sheets

METHODS OF TREATING INFLAMMATION USING SELECTION BINDING COMPOUNDS

CROSS-REFERENCE

This application is a continuation-in-part of our earlier filed application Ser. No. 07/683,458 filed Apr. 11, 1991, now U.S. Pat. No. 5,211,937, issued May 18, 1993, which is a continuation-in-part of our earlier application Ser. No. 07/637,868, filed Jan. 7, 1991, now U.S. Pat. No. 5,143,712, issued Sep. 1, 1992, which is a continuation in part of our earlier filed (now abandoned) application Ser. No. 07/613,113, filed Nov. 15, 1990, which is a continuation in part of our earlier application Ser. No. 07/559,836, filed on Jul. 30, 1990, now U.S. Pat. No. 5,211,936, issued May 18, 1993, all of which applications are incorporated herein by reference and to which applications we claim priority under 35 USC §120. This application is also related to and incorporates by reference in its entirety our earlier filed PCT application PCT/US91/05416 filed Jul. 30, 1991 to which application we claim priority, to the extent allowed, under 35 USC §119 and/or 365.

FIELD OF THE INVENTION

This invention relates generally to determining the presence of and relieving the effects of inflammation. More specifically, this invention relates to carbohydrate ligands which bind to selectins such as leukocyte endothelial cellular adhesion molecule—(hereinafter LECAM-1) and endothelial leukocyte adhesion molecule-1 (hereinafter ELAM-1) and to compositions containing such ligands which are useful, for example, in (a) determining the presence of selectins, (b) assaying for areas of inflammation, and (c) relieving inflammation by blocking the effects of selectins.

BACKGROUND OF THE INVENTION

While protein-protein interactions in cell recognition have been recognized for some time, only recently has the role of carbohydrates in physiologically relevant recognition been widely considered (See Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated with relatively few gene products, suggesting a plausible mechanism for establishing the information necessary to direct a wide range of cell-cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton, M., et al., *Nature* (1986) 324:459; and Tiemeyer, M., et al., *J. Biol. Chem.* (1989) 263:1671). Further, the question has been raised as to the nature of the leukocyte receptor for ELAM-1 (see Bevilacqua et al. *Proc Natl. Acad. Sci. USA* (1987) 84:9238).

Tumor associated glycolipids have been reported in fetal tissue and a variety of human cancers, including CML cells (Fukuda, M. N., et al., *J. Biol. Chem.* (1986) 261:2376; Magnani, J. L., et al., *J. Biol. Chem.* (1982) 257:14365; Hakomori, S., et al., *Biochem. Biophys. Res. Comm.* (1983) 113:791). This has led to the hypothesis that these structures may be important in many developmental and oncogenic processes (J. L. Magnani et al., *J. Biol. Chem.* (1982) 257:14365). Smaller quantities of most of these carbohydrates can be found in normal human tissue (see Fukushi, Y., et al., *J. Exp. Med.* (1984) 160:506), but until now no function for these structures has been reported.

Adhesion of circulating neutrophils to stimulated vascular endothelium is a primary event of the inflammatory response. Several receptors have been implicated in this interaction, including a family of putative lectins that includes $gp90^{MEL}$ (Leu8), GMP-140 (PADGEM) and ELAM-1 (Gong, J.-G., et al., *Nature* (1990) 343:757; Johnston, G. I., et al., *Cell* (1989) 56:1033; Geoffrey, J. S., and Rosen, S. D., *J. Cell Biol.* (1989) 109:2463; Lasky, L. A., et al., *Cell* (1989) 56:1045). While these receptors each contain a domain with sequence homology to calcium dependent lectins, only $gp90^{MEL}$ has been demonstrated to recognize a carbohydrate (See J. S. Geoffrey et al., *J Cell Biol.* (1989) 109:2463). Endogenous ligands for these receptors have yet to be identified.

ELAM-1 is particularly interesting because of its transient expression on endothelial cells in response to IL-1 or TNF (Bevilacqua, M. P., et al., *Science* (1989) 243:1160). The time course of this induced expression (2–8 h) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding for the ELAM-1 receptor.

Recently, several different groups have published papers regarding ELAM-1 ligands which ligands are also referred to as LECAM-2 ligands. Lowe et al. (1990) *Cell* 63:475–484 demonstrated a positive correlation between the LECAM-2 dependent adhesion of HL-60 cell variants and transfected cell lines, with their expression of the sialyl Lewis x (sLex) oligosaccharide, Neu NAc α2-3Gal-β1-4(Fuc α1-3)-GlcNAc. By transfecting cells with plasmids containing an α(1,3/1,4) fucosyltransferase, they were able to convert non-myeloid COS or CHO lines into sLex-positive cells that bind in an LECAM-2 dependent manner. Attempts to block LECAM-2 dependent adhesion using anti-sLex antibodies were uninterpretable due to the agglutination of the test cells by the antibody. They conclude that one or more members of a family of oligosaccharides consisting of sialylated, fucosylated, lactosaminoglycans are the ligands for the lectin domain of LECAM-2. Phillips et al. (1990) *Science* 250:1132–1135 used antibodies with reported specificity for sLex to inhibit the LECAM-2 dependent adhesion of HL-60 or LEC11 CHO cells to activated endothelial cells. Liposomes containing difucosylated glycolipids with terminal sLex structures inhibited adhesion, while those containing nonsialylated Lex structures were partially inhibitory. Walz et al. (1990) *Science* 250:1132–1135 were able to inhibit the binding of a LECAM-2-lgG chimera to HL-60 cells with a monoclonal antibody directed against sLex or by glycoproteins with the sLex structure, but could not demonstrate inhibition with CD65 or CD15 antibodies. Both groups concluded that the sLex structure is the ligand for LECAM-2.

LECAM-1 is particularly interesting because of its ability to block neutrophil influx (Watson et al., *Nature* (1991) 349:164–167). It was expressed in chronic lymphocytic leukemia cells which bind to HEV (see Spertini et al., *Nature* (1991) 349:691–694). It is believed that HEV structures at sites of chronic inflammation are associated with the symptoms of disease such as rheumatoid arthritis, psoriasis, and multiple sclerosis.

Information regarding the DNA sequences encoding endothelial cell-leukocyte adhesion molecules are disclosed in PCT published application WO90/13300 published Nov. 15, 1990 incorporated herein by reference. The PCT publication cites numerous articles which may be related to endothelial cell-leukocyte adhesion molecules. The PCT publication claims methods of identifying ELAM-ligands, as well as methods of inhibiting adhesion between leukocytes and endothelial cells using such ligands and specifically refers to MILAs which are described as molecules involved in leukocyte adhesion to endothelial cells.

Disclosed herein are compounds having a three-dimensional configuration that enables them to bind to a selectin (LECAM-1 and/or ELAM-1) receptor.

DISCLOSURE OF THE INVENTION

Ligand molecules capable of binding to and interrupting the biological chain of events associated with selectin receptors in the human body and in particular ELAM-1 are disclosed as are pharmaceutical formulations containing such ligand molecules. Antagonist ligand molecules act as biochemical blocking agents by binding to selectins such as ELAM-1 and preventing circulating neutrophils from binding to stimulated endothelial cells, thereby preventing a primary event of the inflammatory response. Agonist ligands have the opposite effect. The ligands of the invention are of the formula:

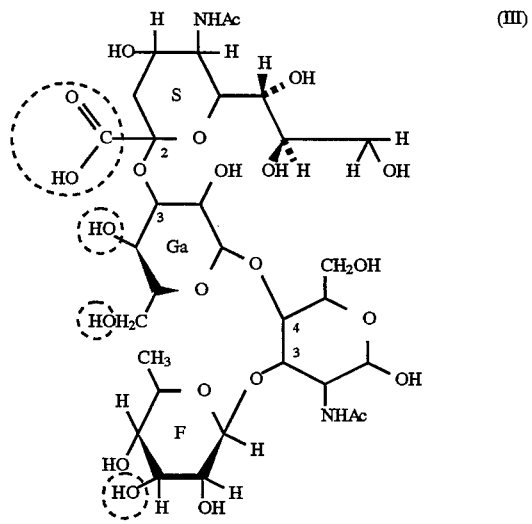

(III)

or molecules which have hydrogen bond donor groups equivalent to the circled groups with respect to their ability to form hydrogen bonds with a selectin under physiological conditions.

These ligands can be bound to anti-inflammatory drugs and/or formulated to provide, for example, compositions useful in assaying a sample for the presence of selectins such as ELAM-1 and/or LECAM-1, compositions useful in detecting the site of inflammation in a patient, or pharmaceutical compositions useful in treating acute inflammation (or treating the inflammatory symptoms of certain diseases) or affecting other phenomena involving the interaction of ELAM-1 on endothelial cells and/or LECAM-1 on circulating neutrophils.

An important aspect of the invention is pharmaceutical compositions which are useful in treating, preventing and/or alleviating any undesirable effects resulting from the interaction of ELAM-1 receptors and circulating neutrophils and/or LECAM-1 receptors and endothelial cells. Such compositions are comprised of an inactive ingredient in the form of a pharmaceutically acceptable excipient material and at least one ligand capable of binding to a selectin receptor.

A primary object of the invention is to provide a selectin ligand in a useful formulation, preferably a pharmaceutical formulation.

Another object is to provide a composition comprising an ELAM-1 and/or LECAM-1 ligand which is preferably labeled and which can be used to assay for the presence of ELAM-1 and/or LECAM-1 in a sample.

Another object is to provide a pharmaceutical formulation containing a selectin ligand which is useful in treating inflammation.

Other objects include providing methods to treat inflammation and to determine the site of inflammation by administering formulations of the type referred to above.

An advantage of the invention is that the ligands are non-toxic saccharide-related compounds with particular functional groups and three-dimensional configurations which allow them to bind selectin receptors effectively and thereby block neutrophils binding to the receptors in numbers per unit of time which result in inflammation and/or other adverse effects.

A feature of the present invention is that the ligands can be labeled and the labeled ligand used in an assay to detect the presence of selectins in a sample.

Other features of the invention include the ability of pharmaceutical formulations of the invention to relieve the inflammatory symptoms of a wide range of diseases which are characterized by the binding of excessive amounts of neutrophils to a site, i.e., an ELAM-1 receptor site.

These and other objects, advantages and features of the present invention will become apparent to those persons skilled in the art upon reading the details of the structure, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

MODES OF CARRYING OUT THE INVENTION

Figure 1:
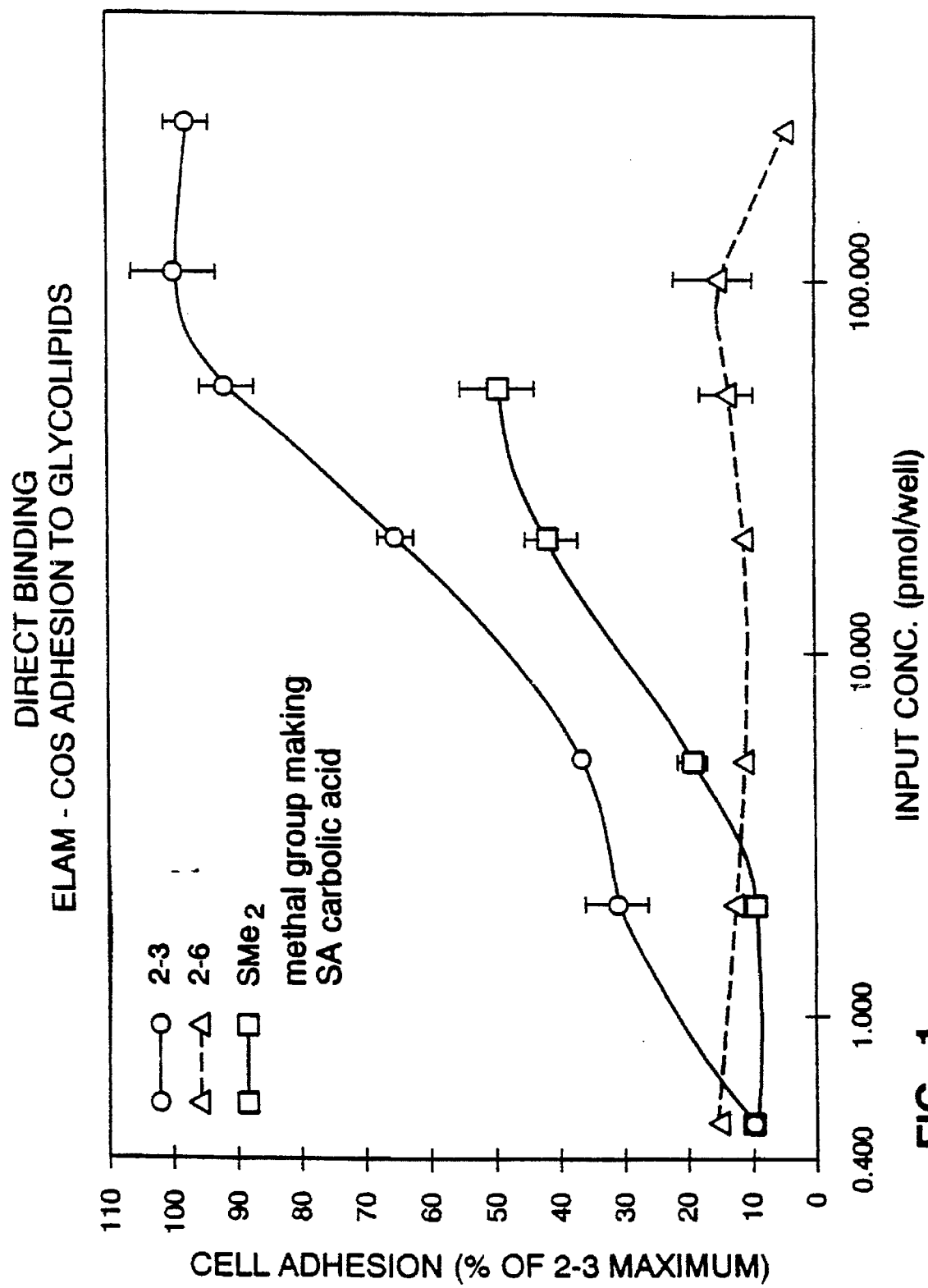
FIG. 1 is a graph showing the results of tests carried out to determine the adhesion of ELAM-transfected COS cells to sialyl-Le$^x$, sialyl-Le$^a$ and sialyl-Le$^x$ methylated at the carboxylic acid group.

Before the present ligands and composition containing such ligands and processes for isolating and using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an" and "the" include plural referents unless the context clearly dictates otherwise. Thus, for example, reference to "a ligand" includes mixtures of ligands, reference to "an ELAM-1" includes reference to mixtures of such molecules, reference to "the formulation" or "the method" includes one or more formulations, methods and/or steps of the type described herein and/or which will become apparent to those persons skilled in the art upon reading this disclosure and so forth.

Some standard abbreviations used in connection with the present invention include: BSA, bovine serum albumin; DEAE, diethylaminoethyl; DMSO, dimethyl-sulfoxide; ELAM-1, endothelial/leukocyte adhesion molecule-1; HPTLC, high performance thin layer chromatography; LECAM-1, leukocyte/endothelial cell adhesion molecule-1; MOPS, 3-[N-Morpholino]propanesulfonic acid; NANA, N-acetylneuraminic acid; PVC, polyvinylchloride; TLC, thin layer chromatography; TFA, trifluoroacetic acid; Tris, tris (hydroxymethyl) aminomethane.

A. General Overview which presents hydrogen bond donor groups in a configuration as per FIG. 3 can block ELAM-1 and LECAM-1 selectins.

It is known that for an acute inflammatory response to occur, circulating neutrophils must bind to and penetrate the vascular wall and access the site of injury. Several molecules have been implicated in this interaction, including a family of putative carbohydrate ligands and their receptors. One molecule that we previously identified is the endogenous carbohydrate ligand for endothelial leukocyte adhesion molecule-1 (hereinafter ELAM-1). The present invention provides a family of ligands that fill this role and which block other selectin receptors.

An adhesion assay described further below was used to obtain a mixture of molecules which adhere to ELAM-1. The invention encompasses those isolated molecules and variations thereof which adhere to ELAM-1 in this assay to the same or a greater degree as compared with ligands isolated. In addition to their ability to adhere to ELAM-1 in this assay, the ligands can be generally characterized by including a saccharide-related unit having at least one fucose residue (or structural and functional equivalent thereof) connected and a sialic acid residue (or structural and functional equivalent thereof). Two embodiments are NeuAc ($\propto$2,3)Gal($\beta$1,3)[Fuc($\propto$1,4)]GlcNAc and NeuAc($\alpha$2,3)Gal ($\beta$1,4)[Fuc$\alpha$1,3]GlcNAc.

Compounds of the invention which adhere to ELAM-1 are encompassed by the following general structural formula I.

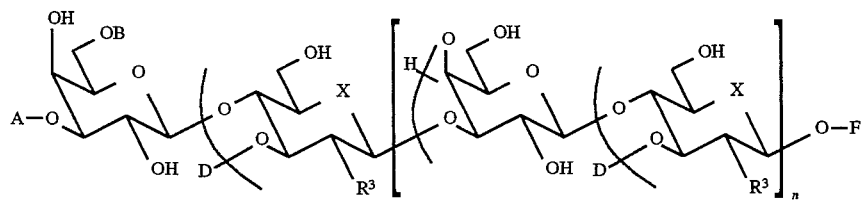

Figure 5:
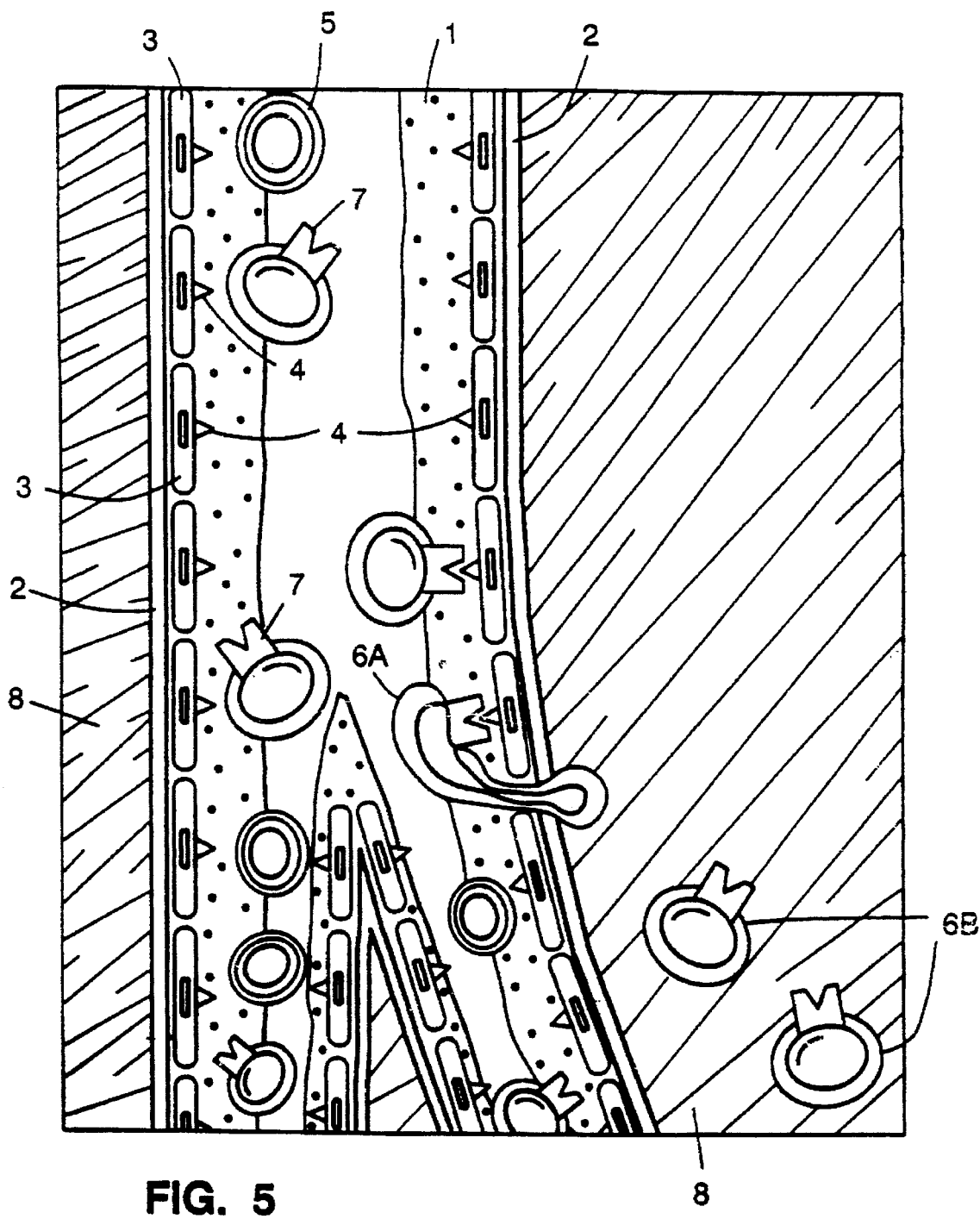
FIG. 5 is a cross-sectional schematic view showing the interaction between white blood cells and activated endothelial cells.

Referring now to FIG. 5, a cross-sectional view of a blood vessel 1 is shown. The vessel wall 2 is lined internally with endothelial cells 3. The endothelial cells 3 can be activated causing the cells 3 to synthesize ELAM-1 which is displayed in FIG. 5 as a triangular surface receptor 4. Both red blood cells 5 and white blood cells 6 flow in the vessel 1. The white blood cells 6 display carbohydrate ligands 7 which have chemical and physical characteristics which allow the ligands 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 6:
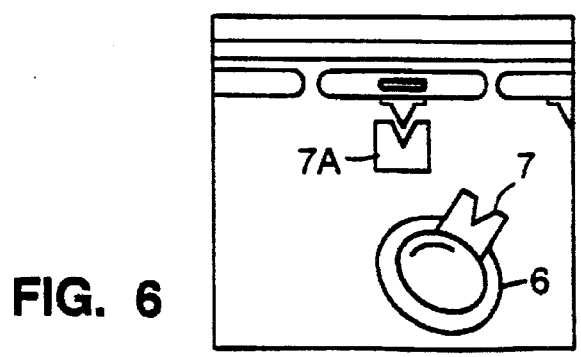
FIG. 6 is a cross-sectional schematic view showing how ligands of the invention might be used as pharmaceuticals to block ELAM-1.

An important aspect of the present invention can be described by referring to FIG. 6. These ligands of the invention, 7A adhere to ELAM-1 by themselves and can be formulated into pharmaceutical compositions, which when administered will effectively block the ELAM-1 and prevent the adhesion of a receptor 7 connected to a white blood cell 6. By administering pharmaceutically effective amounts of ligands 7A, some, but not all, of the white blood cells will not reach the surrounding tissue 8. By slowing the rate at which the white blood cells reach the surrounding tissue, inflammation can be prevented and/or alleviated.

Figure 7:
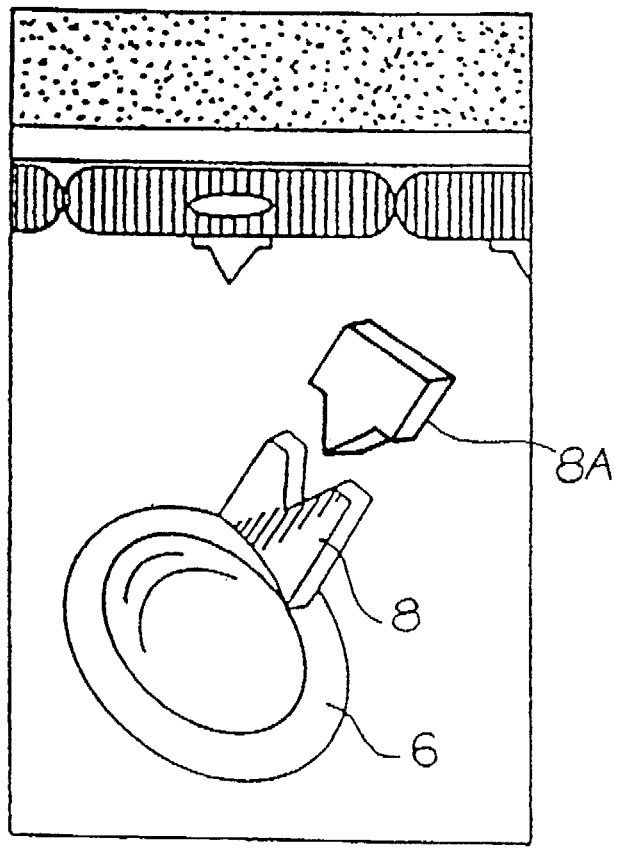
FIG. 7 is a cross-sectional schematic view showing how ligands of the invention might be used as pharmaceuticals to block LECAM-1.

Another important aspect of the invention can be described with reference to FIG. 7. In FIG. 7 the LECAM-1 receptor 8 on the white blood cell 6 is blocked by the ligand 8A. The present inventors have found that a given ligand In Formula I, each of the saccharide rings shown is connected at its 1-position to the next saccharide ring at its 3-position or 4-position and wherein the variables are defined as follows:

At least one of A and B is

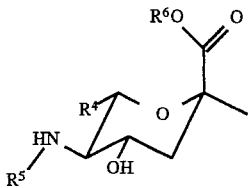

and the other is H, wherein $R^4$ is —(CHOH)$_3$H, H, alkyl containing 1 to 6 carbons, CHO, or perfluoroalkyl containing 1 to 6 carbons;

$R^5$ is selected from the group consisting of H, alkyl containing 1 to 6 carbons, COCH$_3$, COCH$_2$OH, COCF$_3$; and $R^6$ is selected from the group consisting of H, and an alkyl containing 1 to 6 carbons;

each D is independently H, a galactosyl or fucosyl wherein at least one D is $\alpha$-fucosyl connected to the 3-position or 4-position of the sugar to which it is bound;

each $R^3$ is independently OH or NAc;

n is an integer of from 0 to 10 with the proviso that if n is 0 and F is H, $R^3$ is OH;

F is H, a ceramide residue, or comprises a linking group or a solid support or a pharmaceutically active drug;

X is selected from the group consisting of O, S, and $NR^6$ and in the saccharide at the reducing terminus, X may also represent the corresponding dicarbinol at C-1 and C-5.

The ligands of the invention which are bound specifically to ELAM-1 may be linked, as shown, on the reducing terminus to additional substituents. For use in pharmaceutical compositions, the embodiment of F shown in the structural formula I, $F^1$ is generally H, ceramide, or comprises a linking group and/or a pharmaceutically active drug. When used as an analytical tool, the embodiment of F, $F^2$, generally comprises a linking group and/or a solid support. The ligands of formula I may also be labeled using standard radioactive, fluorescent, enzymic or other label for analytical or diagnostic purposes. In general, the significant portion of the compounds of formula I is the ligand shown; the embodiments of the substituent F will depend on the intended use. Suitable embodiments for this substituent will be apparent to those of skill in the art.

Preferred embodiments of the ligands of the invention are those wherein the substituent represented by A or B is an N-acetylneuramyl residue. Especially preferred are those embodiments wherein A is the N-acetylneuramyl residue and B is H.

Also preferred are those embodiments wherein all X are oxygen, or wherein at most one X is converted to the dialcohol at C1 and C5. Also preferred are those embodiments wherein all $R^3$ are —NHAc or wherein at most one or two $R^3$ are OH. Also preferred are those embodiments wherein a D residue proximal to the sialyl residue at the nonreducing terminus is an α-fucosyl residue. By "proximal" is meant within the first two lactosamyl or analogous disaccharide residues.

The present inventors carried out repeated assays and analyzed the results to determine the smallest structural unit which would effectively bind to ELAM-1 and found the following tetrasaccharide, with reactive groups shown in dashed circles.

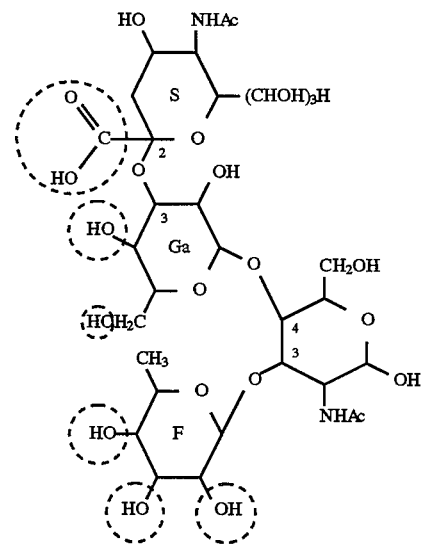

The structural formula shown above can be formulated with a pharmaceutically acceptable carrier in order to provide a preferred composition of the present invention. This composition can be administered (preferably by IV) to treat a variety of conditions (e.g. inflammation) as discussed herein.

Figure 2:
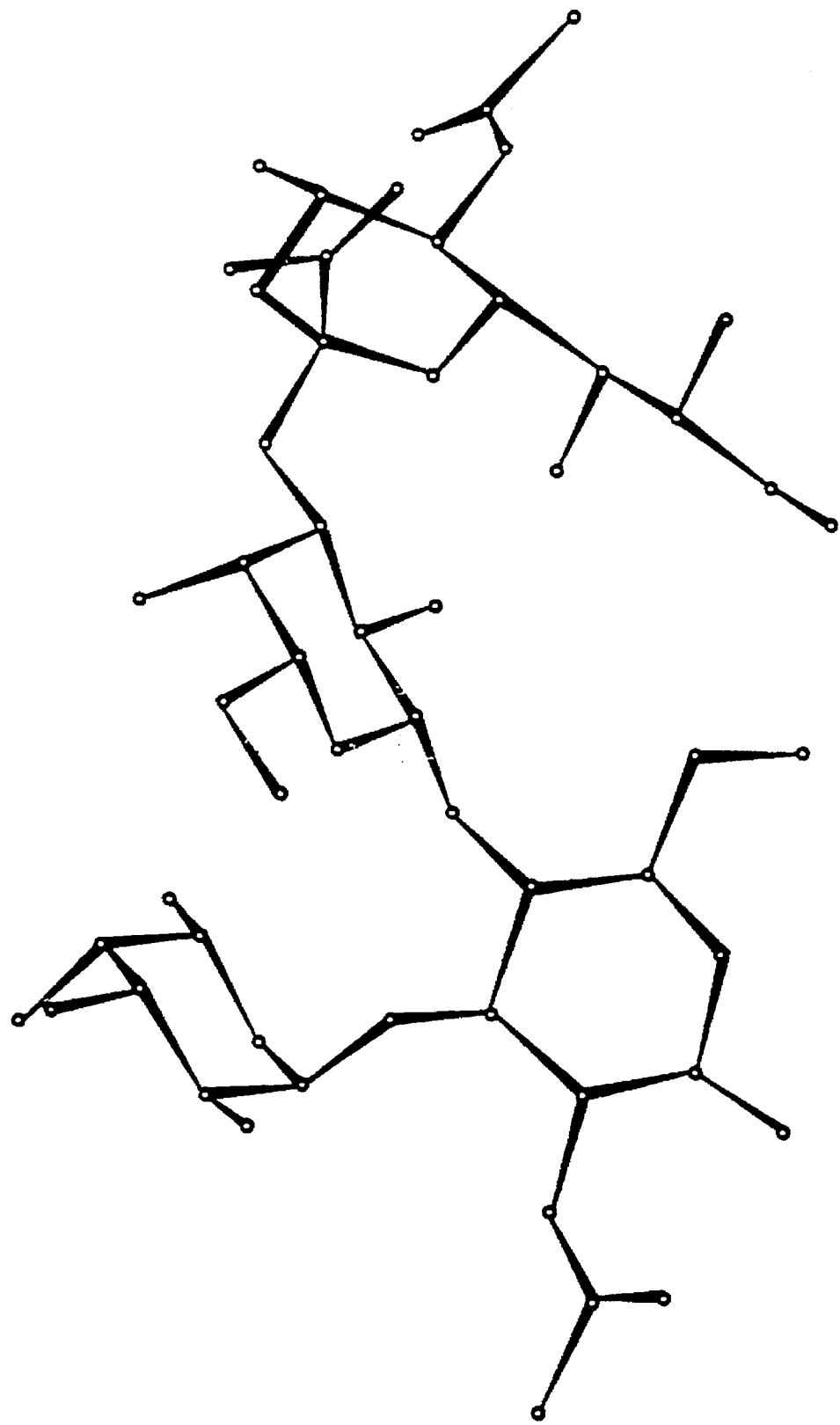
FIG. 2 is a computer generated schematic diagram of the energetically preferred conformation of sialyl-Le$^x$.
Figure 3:
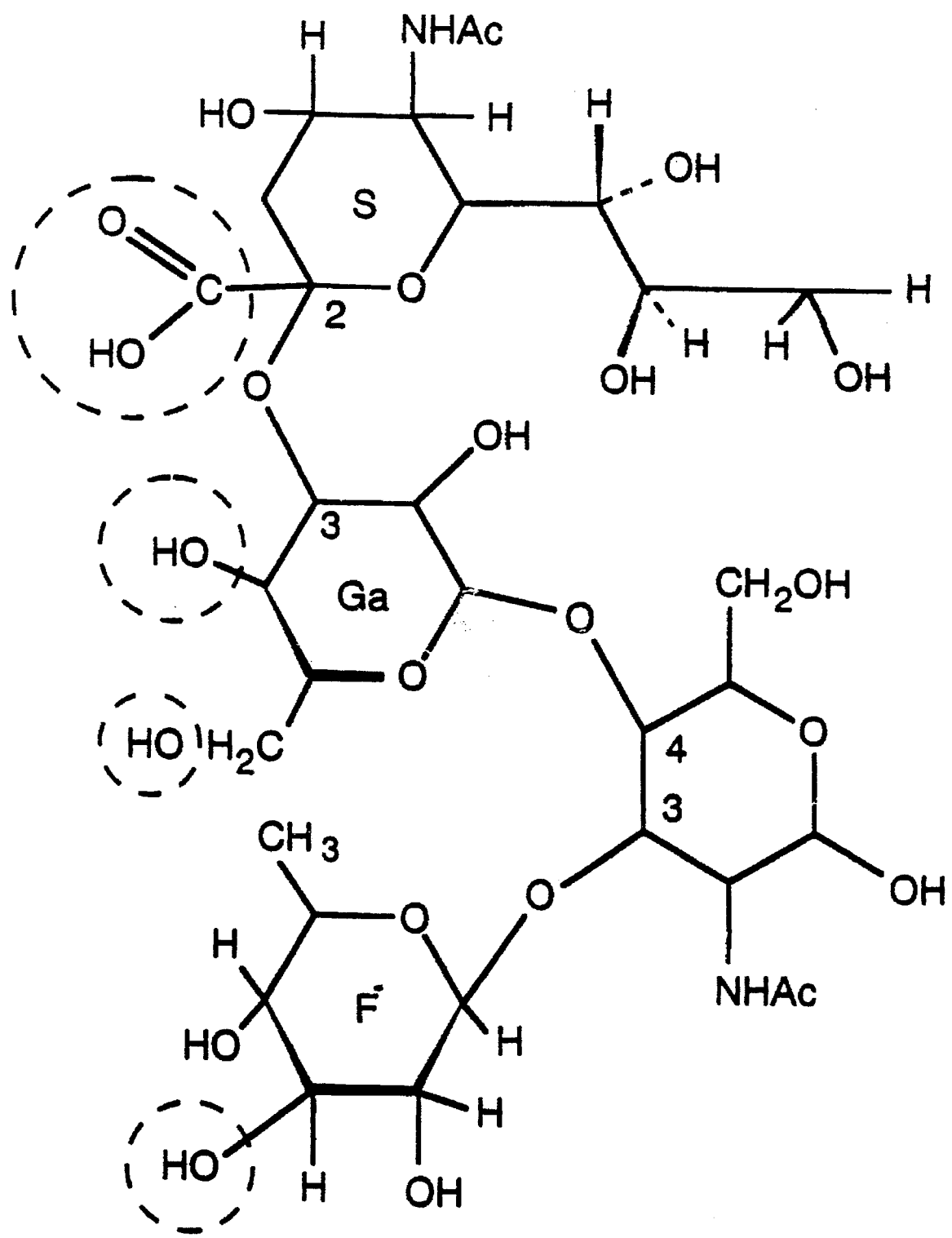
FIG. 3 is a schematic diagram of the structure of sialyl-Le$^x$ showing the hydrogen bond donor positions circled.
Figure 4:
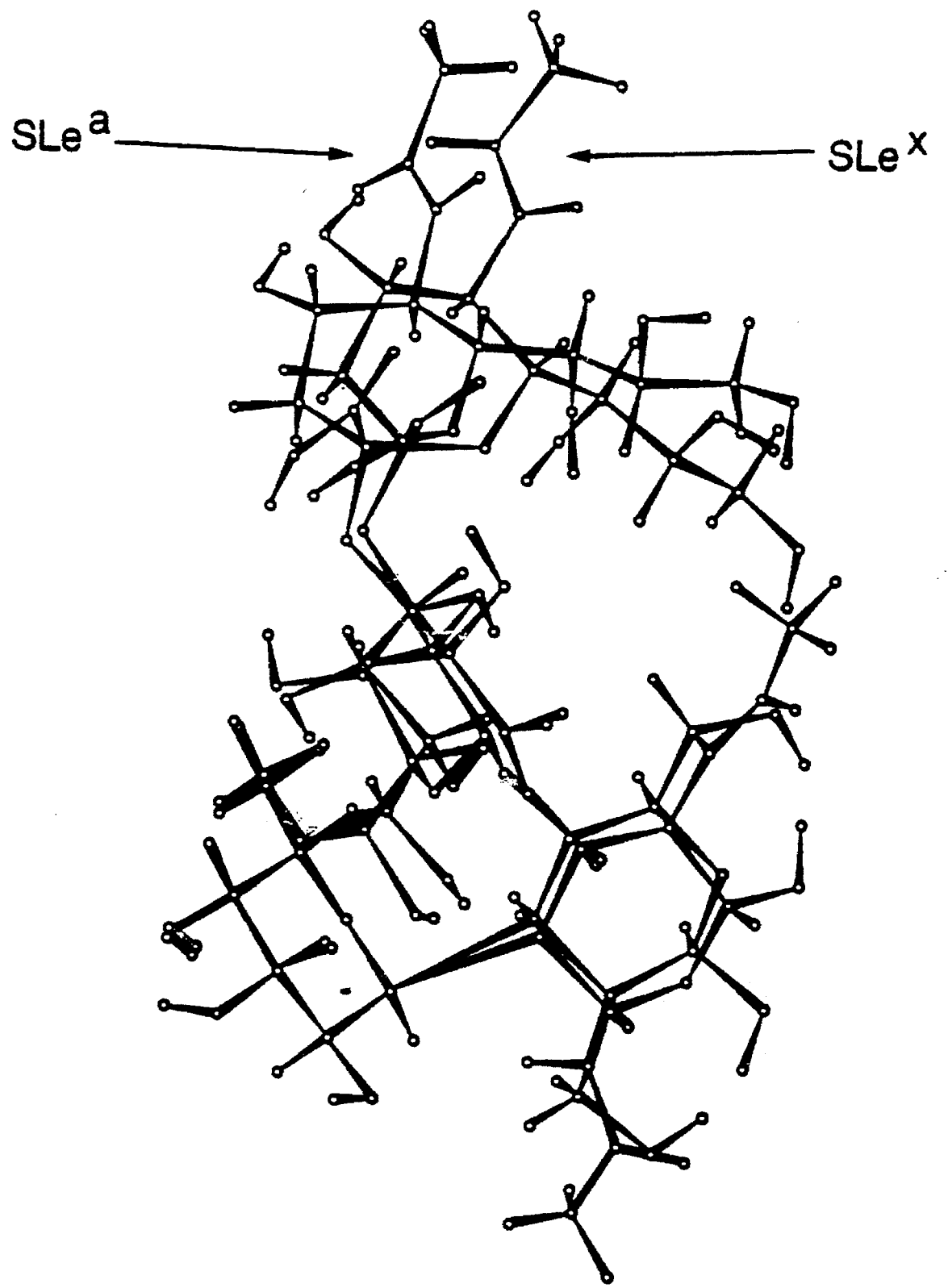
FIG. 4 is a computer generated schematic diagram of the energetically preferred conformations of sialyl-Le$^x$ and sialyl-Le$^a$ superimposed on each other for maximum match to show closeness of fit.

The importance of the above structural formula (shown in FIG. 3) can be further understood when considered in view of the computer generated schematic. diagram shown in FIG. 3. FIG. 3 shows the most stable and therefore most prevalent and preferred conformation of the compound shown in FIG. 2. In order for a ligand of the invention to bind to a selectin receptor such as an ELAM-1 receptor the ligand need not include the identical atoms in the identical configuration as per FIG. 3 but must have (1) a stable three dimensional conformation as per FIG. 2 or (2) a substantially equivalent configuration to that shown in FIG. 2. The equivalency of any other ligand will relate to its physical three dimension structure and the electson configuration of the molecule and in particular the charge related characteristics presented by the functional groups which are circled in FIG. 3. In order for a molecule of the invention to have a substantially equivalent structure to that shown in FIG. 3 the molecule must bind to a selectin receptor (e.g. an ELAM-1 receptor) to the same degree or greater as the ligand of FIG. 3 when the molecule is allowed to bind to the receptor under physiological conditions. The binding of any ligand to any selectin receptor will occur due to hydrogen binding. Accordingly, substantially equivalent ligands will present hydrogen bond donor groups of the same type as the circled groups of FIG. 3. Further, the equivalent ligands will present the donor groups at positions shown in FIG. 2 or positions close enough to those of FIG. 2 to allow for the formation of hydrogen bonding between the ligand and receptor which bonding is the same as or greater than the bonding of a compound of FIG. 3 with a selectin receptor.

The invention also includes a method of assaying candidate ligands for their ability to adhere to ELAM-1. The method comprises attaching candidate ligands to a substrate surface and then contacting the substrate surface thereon with recombinant cells, that are genetically engineered to express high levels of ELAM-1, for a sufficient time to allow the cells to adhere to the substrate bearing the candidate ligand. Thereafter, centrifugal force or other appropriate methodology is applied so as to separate away the cells which do not adhere to the substrate. Candidate ligands which adhere to ELAM-1 are determined via the labels on the cells. Such molecules are isolated, characterized, and their structure specifically identified. Accordingly, the invention also includes glycolipid ligands which can be isolated via such an assay procedure.

B. Assay to Identify Ligand (General)

Radiolabeled COS cells expressing cell surface ELAM-1 were used as probes to screen human leukocyte-derived glycolipids. ELAM-1 transfected COS cells adhered to a subset of sialylated glycolipids which were resolved on TLC plates or adsorbed on PVC microtiter wells. Adhesion to these glycolipids required calcium, but was not inhibited by heparin, chondroitin sulfate, keratin sulfate, or yeast phosphomannan (PPME). Monosaccharide composition, linkage analysis, and FAB mass spectrometry of the purified glycolipids indicated that the ligands for ELAM-1 share common structural characteristics including those indicated above.

In addition to the characteristics noted above, further structural characteristics were found by which ELAM-1 ligands could be identified. These include the presence of the functional groups identified in formula (Ia) by the dotted lines. When these functional groups are present and positioned in space in approximately the same manner as are the groups of formula (I), then the compound will bind to ELAM-1.

One mechanism by which glycolipids could mediate intercellular events would involve the recognition of the glycolipid oligosaccharide moiety on one cell (e.g., an endothelial cell) by a specific carbohydrate-binding protein (lectin) on an opposing cell (e.g., a leukocyte). Data generated in connection with the present invention indicate that acidic glycolipids isolated from leukocytes and ELAM-1 function as such an oligosaccharide-lectin pair, participating in the interaction of neutrophils with the surface of cells of activated vascular endothelium. Many protein-protein interactions have been implicated in neutrophil-endothelium transmigration (see Lo, S. K., et al., *J. Immunol.* (1989) 143:3325; Osborn, L., et al., *Cell* (1989) 59:1203; Larsen, F., et al., *Cell* (1989) 59:305; and Arnaout, M. A., *Blood* (1990) 75:1037). While not wishing to be bound to any theory, the present inventors believe it is likely that this lectin-carbohydrate interaction is only one step in a series that result in neutrophil extravasation.

The adhesion of ELAM-1 for glycolipids described here has been tested. Accordingly, such glycolipids are believed to be useful in mediating a specific, but possibly weak adhesion that is then stabilized and elaborated by the participation of other receptors. Oligosaccharides with the structural and functional characteristics described herein, or modifications of these structures, are believed to be capable of blocking the interaction of neutrophils with activated vascular endothelium mediated by ELAM-1, and hence provide useful pharmaceutically active agents which can interrupt the adverse effects involved in the interaction of ELAM-1 and circulating neutrophils, e.g., prevent or reduce inflammation.

C. Identification of Putative ELAM-1 Ligands Using Recombinantly Produced Receptor A complete cDNA for the ELAM-1 receptor was obtained by PCR starting with total RNA isolated from IL-1 stimulated human umbilical vein endothelium. The resulting cDNA was inserted into the CDM8 plasmid (see Aruffo, A., and Seed, B., *Proc. Natl. Acad. Sci. USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua, M. P., et al., *Science*, (1989) 243:1160; Polte, T., et al., *Nucleic Acids Res.* (1990) 18:1083; Hession, C., et al., *Proc. Natl. Acad. Sci. USA* (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, which is incorporated herein by reference).

COS cells, expressing membrane-bound ELAM-1, were metabolically radiolabeled with $^{32}PO_4$ and used as probes in two assay systems to screen for recognition of glycolipids. In the first, glycolipids were adsorbed to the bottoms of PVC microtiter wells, while in the second they were resolved on TLC plates. In both assays these glycolipids were probed for their ability to support adhesion of ELAM-transfected COS cells, untransfected COS cells, or COS cells transfected with a plasmid containing an irrelevant cDNA, under conditions of controlled detachment force (see Swank-Hill, P., et al., *Anal. Biochem.* (1987) 183:27; and Blackburn, C. C., et al., *J. Biol. Chem.* (1986) 261:2873 each of which is incorporated herein by reference to disclose the details of such assaying methodology).

The glycolipids used in these adhesion experiments were derived from leukocytes collected from patients with chronic myelogenous leukemia (CML) undergoing therapeutic leukopheresis. Denatured cellular material equivalent to about 500 ml of packed cells was extracted and partitioned by the method of Fredman and Svennerholm (Svennerholm, L., and Fredman, P., *Biochem. Biophys. Acta* (1980) 617:97 which is incorporated herein by reference to disclose such methodology). Glycolipids partitioning into the upper phase were freed of phospholipids by saponification and extraction. Glycolipids from the saponified upper phase, containing approximately 100 µmol sialic acid, were initially screened for ELAM-mediated cell adhesion. Up to 25% of the ELAM-transfected COS cells adhered to the crude upper phase glycolipid mixture adsorbed to the bottom of PVC microtiter wells. Cell adhesion directly to glycolipids resolved on TLC plates revealed specific recognition of several relatively polar bands that stained with resorcinol.

D. Separating and Isolating Putative Glycolipid ELAM-1 Ligands

Since the initial screening suggested that ELAM-1 recognized ligands may be acidic glycolipids, the total glycolipids were fractionated by charge on a DEAE-Sepharose (acetate form) column (Pharmacia, Fast Flow). The material not retained on the column and in fractions eluted by step-wise increases in salt concentration (from 5 mM to 250 mM potassium acetate in methanol) were screened for cell adhesion. Virtually all of the ELAM-1 binding activity was eluted with 5 mM potassium acetate, suggesting that the carbohydrate ligand was monosialylated (See the above cited and incorporated Svennerholm article for details of such a procedure). Cell adhesion to these glycolipids was completely blocked by the removal of calcium, but was not inhibited by a number of carbohydrates of known structure, including heparin, chondroitin sulfate, keratin sulfate, or yeast phosphomannan (at 100 µg/ml).

E. Characterizing Putative Ligands for ELAM-1 Affinity

The mixture of glycolipids eluting from the DEAE column in 5 mM KOAc was subsequently fractionated by polarity on beaded silica columns (Iatrobead, Iatron Laboratories). Cell adhesion to aliquots of these fractions revealed three peaks of ELAM-1 binding activity that corresponded to the elution positions (as determined by TLC with resorcinol staining) of the previously identified sialylated glycolipids. Fractions from this column, pooled by their ability to support adhesion of ELAM-transfected COS cells, were separated into three active glycolipid bands by a second Iatrobead column. The more polar two of these were each resolved into two bands by preparative TLC in 55:35:20 (n-butanol:ethanol:water), to yield a total of three ELAM-1 recognized bands in addition to several inactive bands. The most prevalent of the active bands (Band 3) was approximately 0.03% of the total sialic acid found in the crude upper phase mixture, and supported adhesion of up to 60% of the input ELAM-transfected COS cells. These same glycolipid bands are present at much lower levels in HL-60 cell glycolipid extracts. Taken together, the present inventors deduced that these data demonstrate that ELAM-1 is a calcium dependent lectin that recognizes a small subset of structurally related acidic glycolipids present on cells of myelocytic lineage.

F. Characterizing the Structure of ELAM-1 Ligand

To characterize the structure of the ligands, monosaccharide composition of the purified glycolipids was performed by acid hydrolysis followed by anion exchange chromatography and quantitation with pulsed amperometric detection (PAD, Dionex Corp.). Linkages were assigned by methylation followed by hydrolysis, reduction, acetylation and gas chromatography with mass detection. FAB mass spectrometry was performed. Data from composition, linkage analysis, and mass spectrometry on the ELAM recognized Band 2 are consistent with the ligand containing at least a tetrasaccharide containing a fucosyl and sialyl residue. Further, analysis of the information obtained allowed ELAM-1 ligands to be characterized as compounds encompassed by the general structural formula I above. A preferred subgroup of the compounds of formula I is encompassed by structural formula II as follows:

a drug with anti-inflammatory characteristics in that the ligand binds to ELAM-1 which is associated with inflammation. Accordingly, NSAID or non-steroidal anti-inflammatory drugs such as naproxen or ibuprofen which act as anti-inflammatory agents could be administered bound to the ligand and could be administered systemically in smaller amounts than usual while obtaining an equivalent effect or even greater anti-inflammatory effect at the site of inflammation. Any other drugs which might be attached include, but are not limited to, antibiotics, vasodilators and analgesics. Such a drug delivery system would reduce any systemic

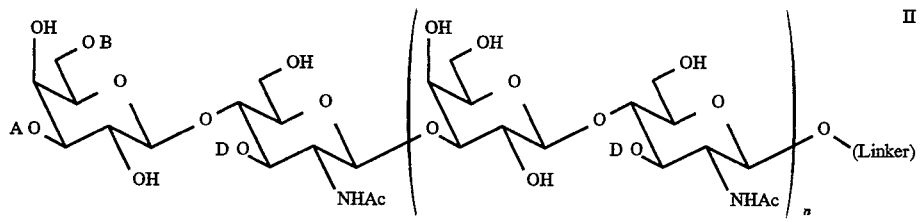

wherein A or B is an N-acetyl neuraminic acid residue and the other is H, each D is independently hydrogen or an α-fucosyl residue with the proviso that at least one D is a fucosyl residue and n is 0, 1 or 2. Additional repeating lactosamine units may be included; F may represent H or a "linker." When F is a linker, it can be any suitable and attachable moiety including a ceramide or a protein or peptide and is preferably a group with a reactive group thereon which allows it to covalently bind to a substrate or pharmaceutically active drug. In one embodiment of the invention the "linker" connects one or more ligands to a support base. The support base is then contacted with a sample to assay for the presence of ELAM-1 in the sample.

The "linker" can be used to attach a pharmaceutically effective drug to the ligand. The (Ligand-Linker-Drug) conjugate thus formed provides an effective drug delivery system for the linked drug. It is especially preferred to attach effect normally caused by the drug in that the drugs could be administered in amounts of one-half to one-tenth the normal dose and still obtain the same anti-inflammatory result at the site of inflammation.

Two specific ligand structures encompassed by formula II are put forth below:

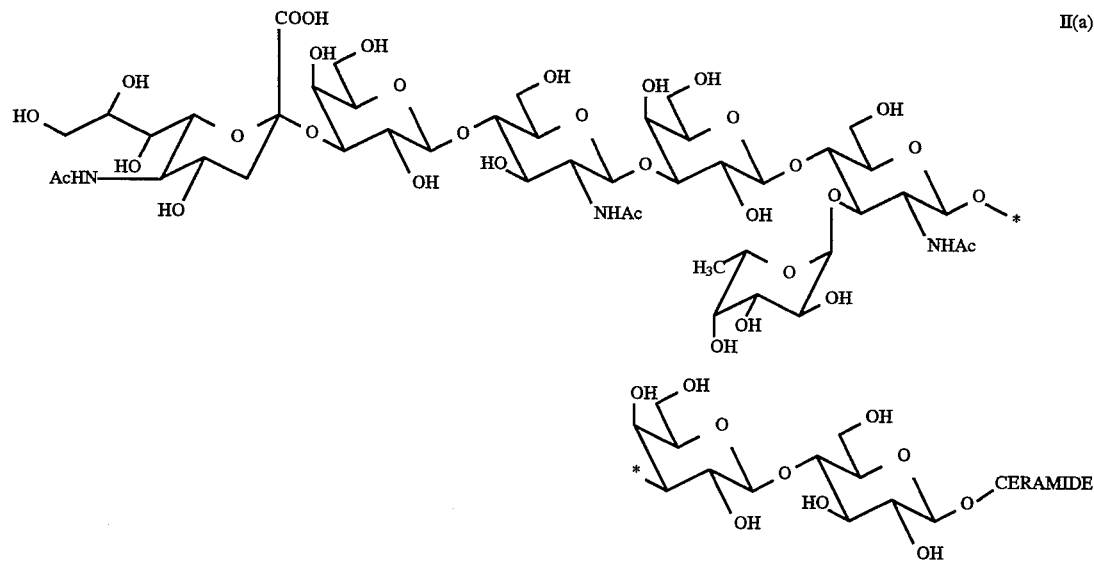

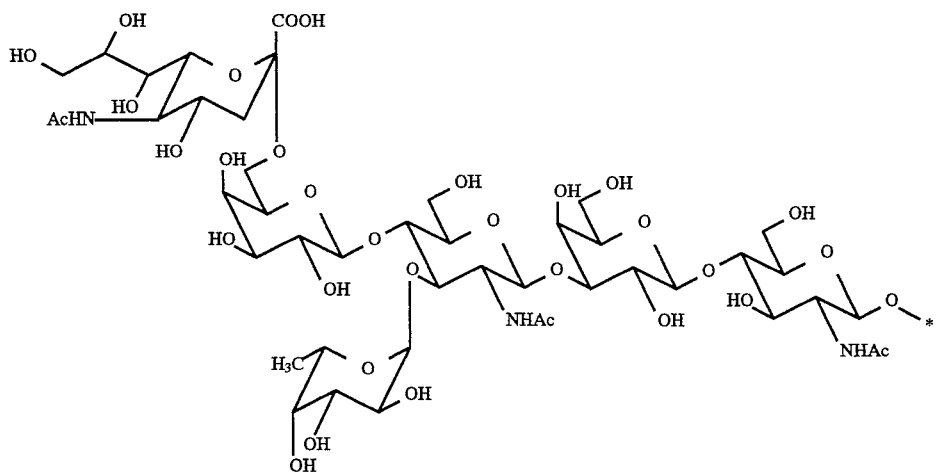

II(b)

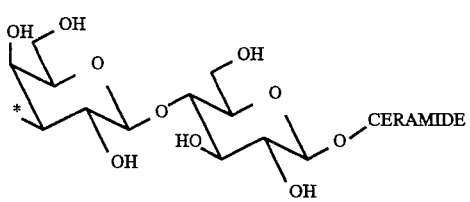

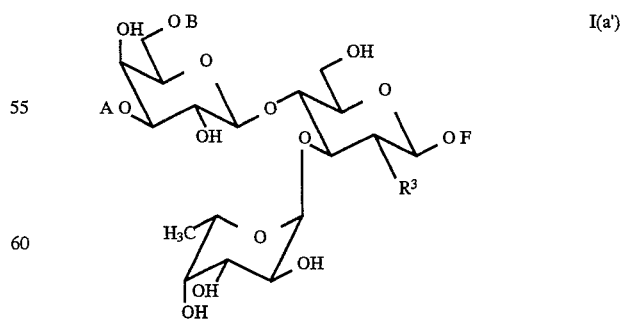

In Formulae II(a) and II(b) the Ac is acetyl and Ac is acetyl throughout this disclosure. Further, the fucose may be present on any of the N-acetyl-glucosamine units and the ceramide is always optionally present. Ceramides are normally present in animal tissue.

The above structures are a lactosyl ceramide with two N-acetyl lactosamine repeating units, a terminal N-acetylneuraminic acid and a fucose on one of the N-acetylglucosamine residues. Composition data for ELAM-recognized Band 2 indicated that there is one fucose for every two glucose residues, with two moles of N-acetyl-glucosamine, and 3 moles of galactose for each mole of glucose. Mass spectrometry reveals a molecular ion at 2027 mass units, with major fragmentation products indicating a loss of a fucose, an N-acetylneuraminic acid, a hexose, an N-acetylhexosamine, hexose, deoxyhexose, N-acetylhexosamine, hexose, and hexose to the ceramide.

Both the composition and the relative ratios of the mass ions at 2027 and 1881 suggest that the specific material tested was a mixture of two components, identical but for the presence of a fucose on 30–40% of the molecules. Data for the other active bands indicate that they are structurally related, varying in the number of the disaccharide repeating units, but each with a terminal unit with a single N-acetyl neuraminic acid residue, and wherein the molecule includes at least one fucose residue attached to one of the disaccharide units.

The structure of one of the nonbinding bands has been characterized and found to contain an identical carbohydrate structure to band 2, but lacking the fucose residue. A second glycolipid that is not recognized by ELAM-1 also lacks fucose. Therefore, it appears that the fucose or a structurally related residue connected to the disaccharide is essential for binding activity, such appears to be true whether the ligand includes 4 or 6 monosaccharides.

Linkage analysis on ELAM-recognized bands 3 and 5 reveal that the glucose residue is substituted at the 4 position, the galactose at the 3 position and the N-acetylglucosamine is a mixture of 4 substituted and 3,4 disubstituted residues. Treatment of the mixed glycolipids with mild acid under conditions that selectively cleave sialic acid and fucose (Dahms, N. M., and Schnaar, R. L., *J. Neurosci.* (1983) 3:806), eliminates ELAM-COS binding, confirming the requirement for these sugars. Taken together, these data indicate that the ligands for ELAM-1 are glycolipids consisting of lactosyl ceramide and N-acetyl lactosamine repeats, with a terminal N-acetyl neuraminic acid residue and a fucose branch on one of the N-acetylglucosamine residues.

The above specific information indicated that a ligand will include (a) one or more repeating units of N-acetyl lactosamine (b) an N-acetyl neuraminic acid residue which is (c) connected to the galactosyl residue of an N-acetyl lactosamine via a 2–3 linkage (II(a)) or a 2–6 linkage (II(b)); and (d) includes at least one fucose residue linked via a 1–3 linkage to N-acetylglucosamine. Further, the ligand can include large numbers of disaccharide units (e.g., 10), but preferably include 2 or 3 disaccharide units. Such ligands include those of general structural formula I put forth above.

General structural formula I encompasses the specific structure of formula Ia and a preferred group of ligands when n is 0 as follows:

I(a')

wherein $R^3$ is OH or NHAc, one of A and B is hydrogen and one is an N-acetyl neuraminic acid residue and F is hydrogen or a linker. Especially preferred are those embodiments wherein A is an N-acetyl neuraminic acid residue.

One preferred carbohydrate compound to be modified for use in the invention is sialyl-Le$^a$ which is a specific saccharide as follows:

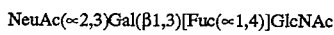

NeuAc($\alpha$2,3)Gal($\beta$1,3)[Fuc($\alpha$1,4)]GlcNAc

Another useful carbohydrate ligand is sialyl-Le$^x$ which is a structural isomer of sialyl-Le$^x$ where the Gal→GlcNAc and Fuc→GlcNAc linkage positions are interchanged. The present inventors have found that such carbohydrate compounds have hydroxyl groups spatially positioned in such a manner that they allow the carbohydrate to bind to a specific receptor on the surface of an activated endothelial cell.

SPECIFIC EXAMPLES OF LIGANDS

Other preferred groups of ligands encompassed by general structural formula I wherein n is 1 are represented by the following subgeneric formulae as follows:

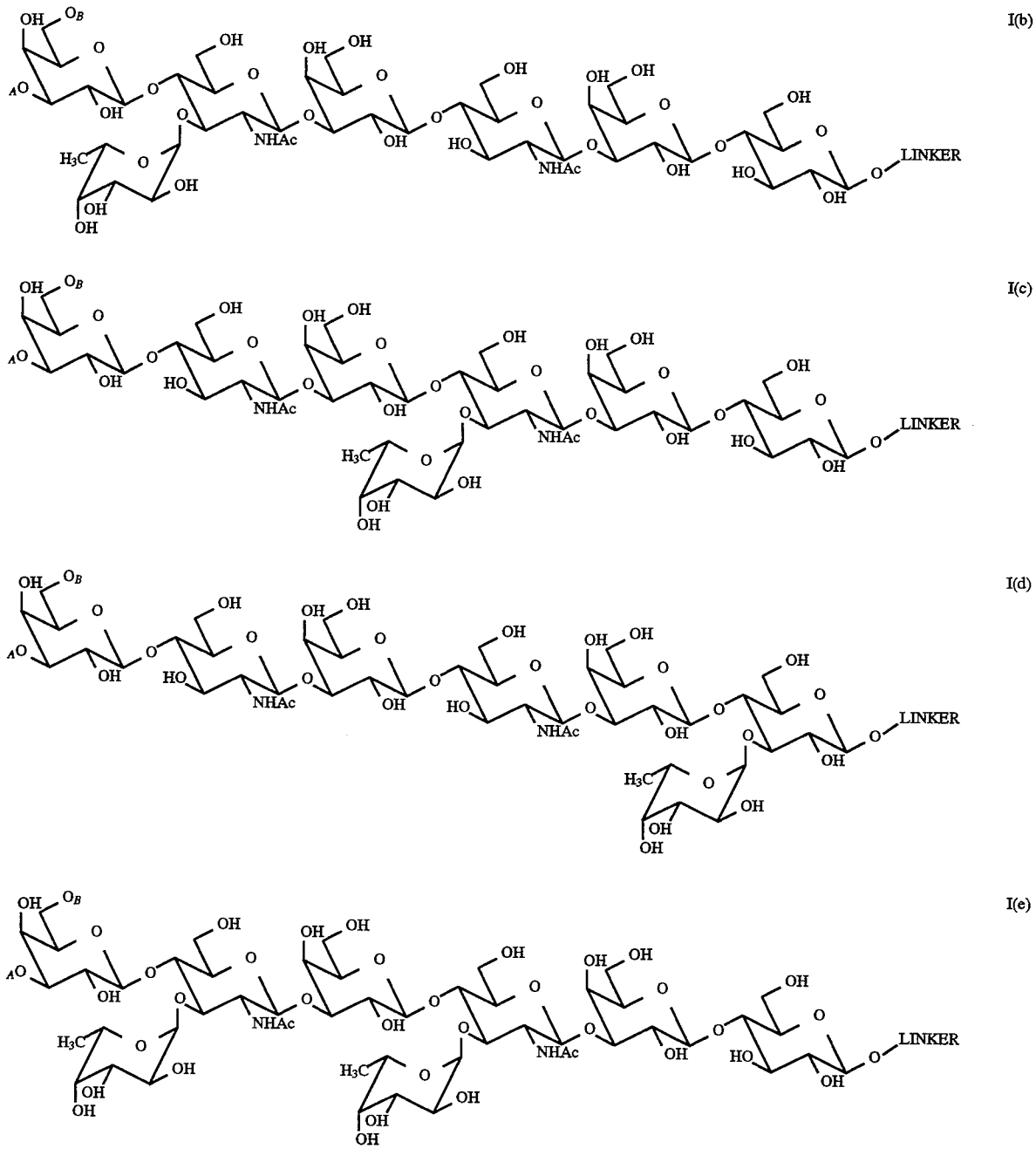

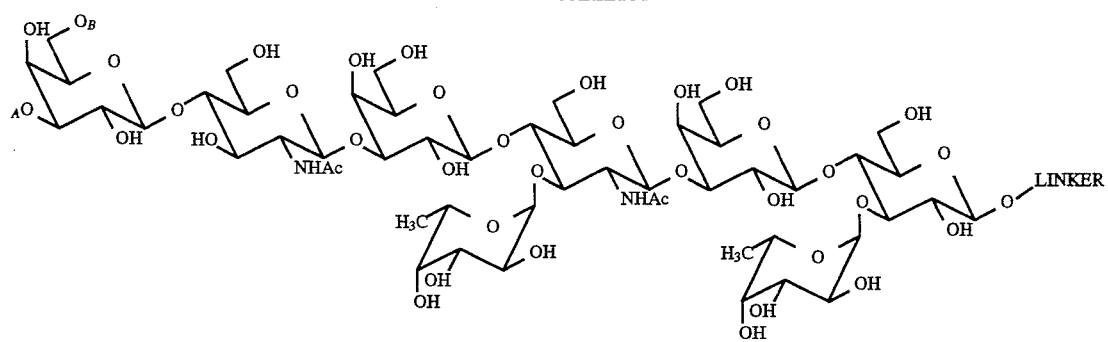
I(f)
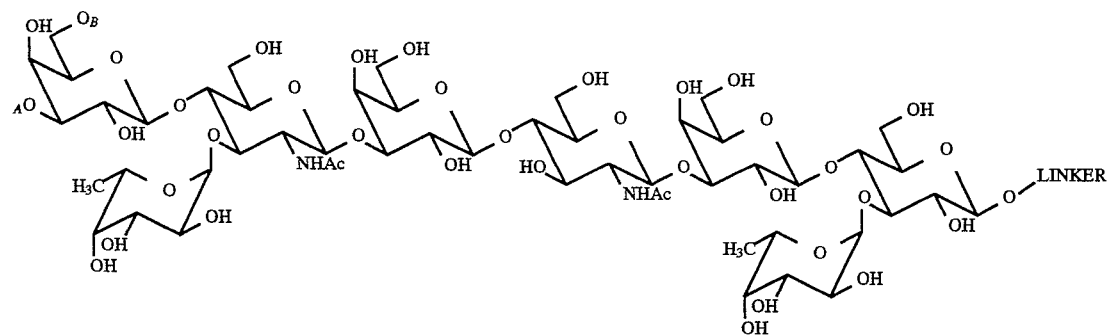
I(g)
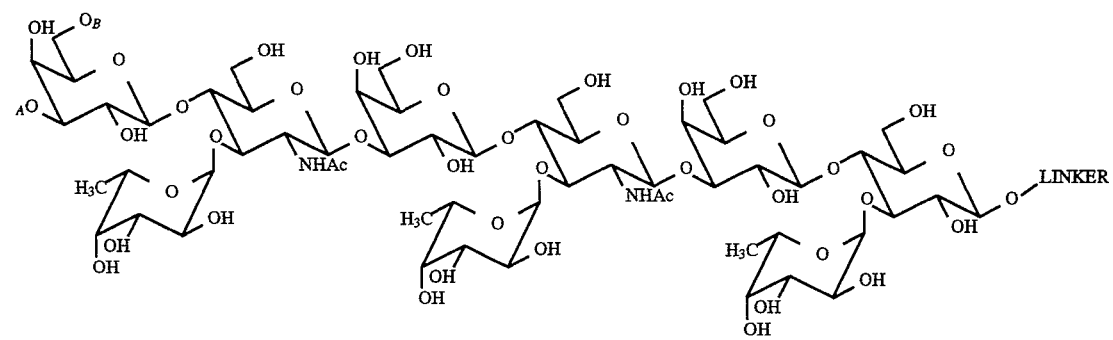
I(h)
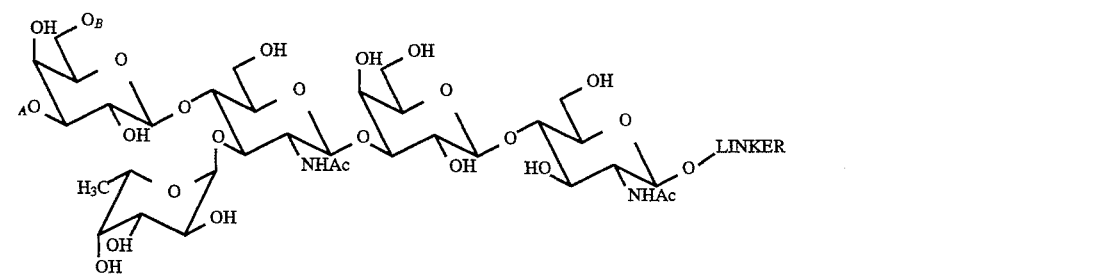
I(i)
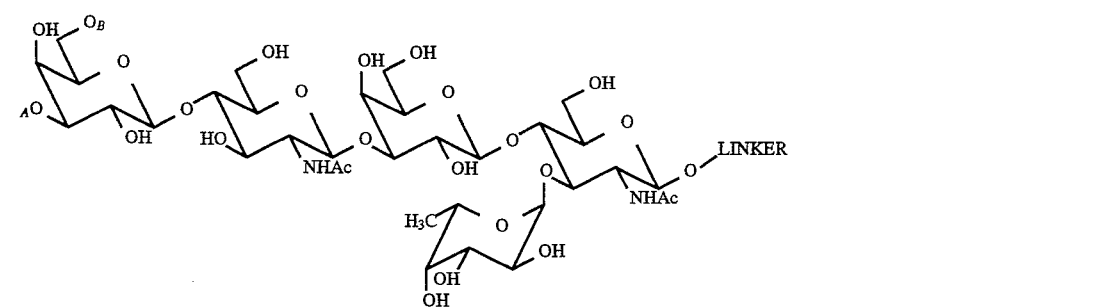
I(j)

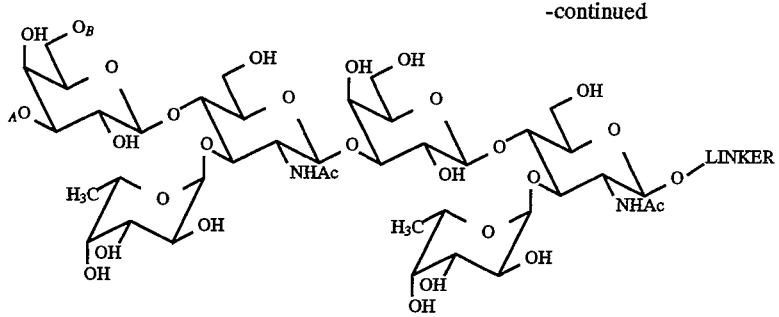

I(k)

Examples of specific ligands of the invention can also be expressed as follows:

NeuNAcα2-3Galβ1-4(Fucα1-3)GlcNAc
NeuNAcα2-6Galβ1-4(Fucα1-3)GlcNAc
NeuNAcα2-3Galβ1-4GlcNAcβ1-3Galβ1-4(Fucα1-3)GlcNAc
NeuNAcα2-6Galβ1-4GlcNAcβ1-3Galβ1-4(Fucα1-3)GlcNAc
NeuNAcα2-3Galβ1-4(Fucα1-3)GlcNAcβ1-3Galβ1-4(Fucα1-3)GlcNAc
NeuNAcα2-6Galβ1-4(Fucα1-3)GlcNAcβ1-3Galβ1-4(Fucα1-3)GlcNAc
NeuNAcα2-3Galβ1-4(Fucα1-3)GlcNAcβ1-3Galβ1-4Glc
NeuNAcα2-6Galβ1-4(Fucα1-3)GlcNAcβ1-3Galβ1-4Glc
NeuNAcα2-3Galβ1-4GlcNAcβ1-3Galβ1-4(Fucα1-3)GlcNAcβ1-3Galβ1-4Glc
NeuNAcα2-6Galβ1-4GlcNAcβ1-3Galβ1-4(Fucα1-3)GlcNAcβ1-3Galβ1-4Glc
NeuNAcα2-3Galβ1-4(Fucα1-3)GlcNAcβ1-3Galβ1-4(Fucα1-3)GlcNAcβ1-3Galβ1-4Glc
NeuNAcα2-6Galβ1-4(Fucα1-3)GlcNAcβ1-3Galβ1-4(Fucα1-3)GlcNAcβ1-3Galβ1-4Glc
NeuNAcα2-3Galβ1-4(Fucα1-3)GlcNAcβ1-3Galβ1-4(Fucα1-3)Glc
NeuNAcα2-6Galβ1-4(Fucα1-3)GlcNAcβ1-3Galβ1-4(Fucα1-3)Glc
NeuNAcα2-3Galβ1-4GlcNAcβ1-3Galβ1-4(Fucα1-3)GlcNAcβ1-3Galβ1-4(Fucα1-3)Glc
NeuNAcα2-6Galβ1-4GlcNAcβ1-3Galβ1-4(Fucα1-3)GlcNAcβ1-3Galβ1-4(Fucα1-3)Glc
NeuNAcα2-3Galβ1-4(Fucα1-3)GlcNAcβ1-3Galβ1-4(Fucα1-3)GlcNAcβ1-3Galβ1-4(Fucα1-3)Glc
NeuNAcα2-6Galβ1-4(Fucα1-3)GlcNAcβ1-3Galβ1-4(Fucα1-3)GlcNAcβ1-3Galβ1-4(Fucα1-3)Glc
NeuNAcα2-3Galβ1-3(Fucα1-4)GlcNAc
NeuNAcα2-6Galβ1-3(Fucα1-4)GlcNAc
NeuNAcα2-3Galβ1-3GlcNAcβ1-4Galβ1-4(Fucα1-3)GlcNAc
NeuNAcα2-6Galβ1-3GlcNAcβ1-4Galβ1-4(Fucα1-3)GlcNAc
NeuNAcα2-3Galβ1-3(Fucα1-4)GlcNAcβ1-3Galβ1-4(Fucα1-3)GlcNAc
NeuNAcα2-6Galβ1-3(Fucα1-4)GlcNAcβ1-3Galβ1-4(Fucα1-3)GlcNAc
NeuNAcα2-3Galβ1-3(Fucα1-4)GlcNAcβ1-3Galβ1-4Glc
NeuNAcα2-6Galβ1-3(Fucα1-4)GlcNAcβ1-3Galβ1-4Glc
NeuNAcα2-3Galβ1-3GlcNAcβ1-4Galβ1-4(Fucα1-3)GlcNAcβ1-3Galβ1-4Glc
NeuNAcα2-6Galβ1-3GlcNAcβ1-4Galβ1-4(Fucα1-3)GlcNAcβ1-3Galβ1-4Glc
NeuNAcα2-3Galβ1-3(Fucα1-4)GlcNAcβ1-3Galβ1-4(Fucα1-3)GlcNAcβ1-3Galβ1-4Glc
NeuNAcα2-6Galβ1-3(Fucα1-4)GlcNAcβ1-3Galβ1-4(Fucα1-3)GlcNAcβ1-3Galβ1-4Glc
NeuNAcα2-3Galβ1-3(Fucα1-4)GlcNAcβ1-3Galβ1-4(Fucα1-3)GlcNAcβ1-3Galβ1-3(Fucα1-4)Glc
NeuNAcα2-3Galβ1-4GlcNAcβ1-3Galβ1-3(Fucα1-4)GlcNAc
NeuNAcα2-6Galβ1-4GlcNAcβ1-3Galβ1-3(Fucα1-4)GlcNAc
NeuNAcα2-3Galβ1-4(Fucα1-3)GlcNAcβ1-3Galβ1-3(Fucα1-4)GlcNAc
NeuNAcα2-6Galβ1-4(Fucα1-3)GlcNAcβ1-3Galβ1-3(Fucα1-4)GlcNAc
NeuNAcα2-3Galβ1-4GlcNAcβ1-3Galβ1-3(Fucα1-4)GlcNAcβ1-3Galβ1-4Glc
NeuNAcα2-6Galβ1-4GlcNAcβ1-3Galβ1-3(Fucα1-4)GlcNAcβ1-3Galβ1-4Glc
NeuNAcα2-3Galβ1-4(Fucα1-3)GlcNAcβ1-3Galβ1-3(Fucα1-4)GlcNAcβ1-3Galβ1-4Glc
NeuNAcα2-6Galβ1-4(Fuα1-3)GlcNAcβ1-3Galβ1-3(Fucα1-4)GlcNAcβ1-3Galβ1-4Glc
NeuNAcα2-3Galβ1-4(Fucα1-3)GlcNAcβ1-3Galβ1-3(Fucα1-4)Glc
NeuNAcα2-6Galβ1-4(Fucα1-3)GlcNAcβ1-3Galβ1-3(Fucα1-4)Glc
NeuNAcα2-3Galβ1-4GlcNAcβ1-3Galβ1-3(Fucα1-4)GlcNAcβ1-3Galβ1-4(Fucα1-3)Glc
NeuNAcα2-6Galβ1-4GlcNAcβ1-3Galβ1-3(Fucα1-4)GlcNAcβ1-3Galβ1-4(Fucα1-3)Glc
NeuNAcα2-3Galβ1-4(Fucα1-3)GlcNAcβ1-3Galβ1-3(Fucα1-4)GlcNAcβ1-3Galβ1-4(Fucα1-3)Glc
NeuNAcα2-6Galβ1-4(Fucα1-3)GlcNAcβ1-3Galβ1-3(Fucα1-4)GlcNAcβ1-3Galβ1-4(Fucα1-3)Glc

EXAMPLES OF ISOLATION AND CHARACTERIZATION PROCEDURES

The following examples are provided so as to provide those of ordinary skill in the art with a complete disclosure and description of how to make compounds and compositions of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

EXAMPLE 1

Isolation of Putative ELAM-1 Ligands Via Recombinantly Produced Receptors

Upper phase, saponified neutrophil glycolipids (100 μmol sialic acid) were loaded on a 200 ml DEAE-Sepharose Fast Flow column (Pharmacia) in 4:8:3 (chloroform:methanol:water) washed with three column volumes of methanol, and eluted with 200 ml steps of 5, 10, 20, 50, 100 and 250 mM potassium acetate in methanol (For further details see Blackburn et al., J. Biol. Chem. (1986) 261:2873 which is incorporated herein by reference to describe and disclose such a procedure). Fractions were desalted and aliquots then dried, resuspended in 100% ethanol containing 1 μM phosphatidyl choline and 4 μM cholesterol, and an equal volume of water added. This material was added to PVC microtiter wells (50 μl/well) and the glycolipids adsorbed for 80 min at room temperature (For details on this procedure see Aruffo, Proc. Natl. Acad. Sci. U.S.A., (1987) 84:8573).

A full length cDNA encoding ELAM-1 was obtained by 35 cycles of the polymerase chain reaction with 1 μg of total RNA extracted from IL-1 stimulated human umbilical vein endothelial cells, utilizing primers complementary to the untranslated flanking sequences (5'-GGTGCGGCCGCGGCCAGAGACCCGAGGAGAG-3' and 5'-GGTGTCGACCCCACCTGAGAGATCCTGTG-3'). The 2 Kb insert generated was gel purified, directionally cloned into the mammalian expression vector, CDM8 that had been modified by the insertion of a SalI site into the polylinker, and grown in E. coli (MC1061/p3). Plasmids were isolated from individual colonies and used to transfect COS cells. Putative ELAM-1 encoding plasmids were selected based on the ability of these transfected COS cells to support HL-60 cell adhesion 72 h posttransfection.

A positive cDNA whose sequence corresponded to the published sequence of ELAM-1 with two nucleic acid substitutions was used in all experiments. COS cells were transfected with 1 μg of this plasmid DNA per $3.5-5.0\times10^5$ cells, with 400 μg/ml DEAE-dextran and 100 μM chloroquine for 4 h, followed by a brief exposure to 10% DMSO in PBS. Cells were metabolically radiolabeled overnight with carrier free $^{32}PO_4$ and harvested in PBS supplemented with 0.02% azide and 2 mM EDTA at 72 h post-transfection for use in cell adhesion studies.

The adsorbed lipids were screened for their ability to support adhesion of ELAM-transfected COS cells using a centrifugation assay (described in detail in the above cited Blackburn article). The results demonstrate that the majority of the adhesion-supporting material in the unfractionated neutrophil glycolipids elutes with the 5 mM salt fractions, suggesting a monosialylated glycolipid. The pooled material eluted with 5 mM salt was used in further purification procedures.

EXAMPLE 2

Determining Putative Glycolipid ELAM-1 Ligands

The desalted material eluted from DEAE with 5 mM salt (approximately 11.5 μmols sialic acid) was loaded onto a 100 ml beaded silica column (Iatrobeads, 100 μm bead dia.) in 60:35:8 (chloroform:methanol:water) and eluted isocratically with a gravity feed of the same solvent. Fractions (2.5 ml) were collected, dried and screened for adhesion of ELAM-transfected COS cells by the PVC microtiter well adsorption assay described above in Example 1, or by a TLC overlay procedure. Fractions from the Iatrobead column were pooled based on their ability to support adhesion of ELAM-transfected COS cells in the microtiter assay. These pools were run on High Performance Silica TLC (HPTLC) plates in 60:35:10 (chloroform:methanol:0.25% aqueous KCl). Companion plates were coated with polyisobutyl methacrylate (0.005% in hexane) and probed with ELAM-transfected COS or control COS (metabolically radiolabeled with $^{32}PO_4$) using conditions of controlled detachment force as described in detail in Swank-Hill et al. Anal. Biochem (1987) 163:27 which is incorporated herein by reference. Autoradiographs of a TLC plate probed with ELAM-transfected COS cells was made. The bands of the autoradiographs were compared with control-COS probed autoradiographs. The pools containing the bands recognized specifically by the ELAM-transfected COS cells were taken through further purification.

EXAMPLE 3

Further Purification

Glycolipids at each step of purification were adsorbed to PVC microtiter wells and probed with ELAM-transfected or control COS cells as described in Example 1. Results from a single input glycolipid concentration were shown to demonstrate increased specific binding activity achieved with purification of the glycolipid.

ANALYSIS of RESULTS OBTAINED

The above examples clearly demonstrate that neutrophils possess surface glycolipid molecules which are referred to herein as ligands and which ligands have an affinity for and bind to receptor molecules on the surface of endothelial cells which receptors are referred to herein as ELAM-1. It is also clear that there are a variety of different glycolipid molecules which can act as ligands which adhere to the ELAM-1. The larger molecules extracted which act as ligands do so because they include within their structure a particular molecular configuration required for adhesion to the ELAM-1. The precise degree of variation which might be allowed in such ligands without disturbing their ability to adhere to ELAM-1 is not presently known. However, the above experiments were the first to isolate and characterize groups of molecules which do adhere to ELAM-1 and thereafter specifically identify and characterize the structure of those molecules.

The ELAM-1 ligands of the present invention form hydrogen bonds with receptors on the surface of activated endothelial cells. Without being bound to any particular theory, it is believed that certain groups on the ELAM-1 ligands act as hydrogen bond donors which are spatially positioned in a manner so as to match hydrogen bond acceptors on the activated endothelial cells. Accordingly, molecules which have hydrogen bond donor groups spatially positioned thereon in a manner substantially equivalent to the hydrogen bond donor groups of sialyl-Le$^x$ will bind to activated endothelial cells.

The general structural formula I put forth above encompasses a number of compounds which include characteristic features of isolated compounds which were shown to adhere to ELAM-1 receptors. Based on that general structural formula, the smallest molecular moiety believed to be capable of adhering to ELAM-1 is shown within structural formula I(a). The upper limit on the size of the molecule is not particularly important and may be a molecule wherein n=10, which molecule would include 12 repeating disaccharide units. Larger molecules can also act as ligands provided they include in their structure, the required minimum binding structure. Based on the above experiments, it is also known that the backbone of the polymer which we have shown as repeating disaccharide units must be attached to at least one fucose molecule (or structural and functional equivalent thereof) and further that the terminal disaccharide of the molecule must include a sialic acid residue, preferably an N-acetylneuraminic acid residue (or structural and functional equivalent thereof) connected at either the 3 or 6 position of the terminal saccharide. Variations on the structures may also be possible provided those variations do not alter structural and/or charge-related characteristics which would interfere with the adhesion of the ligand to ELAM-1. Thus, in its broadest sense, the present invention encompasses not only the molecules of general structural formula I but various equivalents thereof which equivalents have an affinity for and an ability to adhere to ELAM-1 to the same or a greater degree than molecules of formula I adhere to ELAM-1. The characteristics of such additional molecules can, of course, be confirmed using the adhesion assay described above in detail and/or related assays which test the adhesion of putative ligand to ELAM-1 under conditions of controlled detachment force. Other such molecules which can be extracted and/or synthesized may be used directly and/or formulated and delivered to a patient so that the ELAM-1 receptors of the patient are blocked, at least to a certain degree, thus preventing the adhesion of the glycolipids on the surface of the neutrophils to ELAM-1 and thereby avoiding the adverse responses (e.g., inflammation) which such neutrophils eventually create.

USE and ADMINISTRATION

The compounds of the invention such as various ligands of structural formula I can be administered to a subject in need thereof to treat the subject by either prophylactically preventing inflammation or relieving it after it has begun. The ligands are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation.

A sufficient amount of ligand molecules should be administered to bind to a substantial portion of the ELAM-1 expected to cause or actually causing inflammation so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

Determining the dose of ELAM-1 ligands to be administered, it must be kept in mind that one may not wish to completely block all of the ELAM-1 receptors. In order for a normal healing process to proceed, at least some of the white blood cells or neutrophils must be brought into the tissue in the areas where the wound, infection or disease state is occurring. The amount of the ELAM-1 ligands administered as blocking agents must be adjusted carefully based on the particular needs of the patient while taking into consideration a variety of factors such as the type of disease that is being treated.

It is believed that the ligands or blocking agents of the present invention can be used to treat a wide range of diseases, including diseases such as rheumatoid arthritis and multiple sclerosis. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of the present invention might also be administered to prevent the undesirable aftereffects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the ELAM-1 receptors within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The ligand molecules of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles. The ligands in the form of glycolipids and carbohydrates or more specifically compounds of formula I can be mixed with compatible, pharmaceutically acceptable excipients.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the ligand molecules adequate to achieve the desired state in the subject being treated.

The various ligand compounds of the present invention can be used by themselves or in combination with pharmaceutically acceptable excipient materials as described above. However, the ligand compounds of the invention can be made as conjugates wherein the compounds of the invention are linked in some manner to a label. By forming such conjugates, the ligand compounds of the invention act as biochemical delivery systems for the label so that a site of inflammation can be detected.

The ligand molecules of the invention could also be used as laboratory probes to test for the presence of ELAM-1 in a sample. Such probes are preferably labeled such as with a radioactive label. There are a number of known labels including radioactive labeled atoms, e.g. radioactive C, O, N, P, or S, fluorescent dyes and enzyme labels which can be attached to ligands of the invention using known procedures. Labels as well as methods of attaching labels to sugar moieties are disclosed in U.S. Pat. No. 4,849,513 issued Jul. 18, 1989 to Smith et al. which patent is incorporated herein by reference to disclose labels and methods of attaching labels.

The instant invention is shown and described herein in what is considered to be the most practical and preferred embodiments. Publications listed herein are incorporated herein by reference to disclose specific procedures on how to make, and/or use the invention. Further, it is recognized that departures may be made therefrom which are within the scope of the invention, and that obvious modifications will occur to one skilled in the art upon reading this disclosure.

What is claimed is:

1. A method of treating inflammation in a patient in need thereof comprising:

administering to said patient a therapeutically effective amount of an injectable pharmaceutical composition comprised of:
a pharmaceutically acceptable carrier; and
a compound selected from the group consisting of:

(a) a compound of formula III

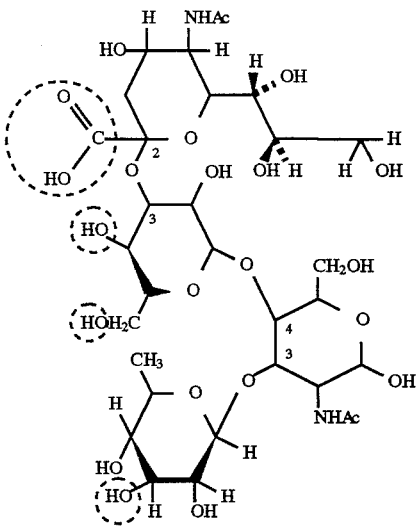

which compound binds to a selectin receptor; and
(b) molecules having hydrogen bond donor groups equivalent to the circled groups of formula III with respect to their ability to form hydrogen bonds with a selectin receptor;

wherein the selectin-binding compound selected from the group consisting and of (a) and (b) is present in the composition in an amount in the range of about 1% to about 95% by weight.

2. The method of claim 1, wherein the patient is a human and the selectin receptor is an ELAM-1 receptor.

3. The method of claim 1, wherein the selected compound is (b) a molecule having hydrogen bond donor groups equivalent to the circled groups of formula III and having an energetically preferred conformation schematically represented by the structure:

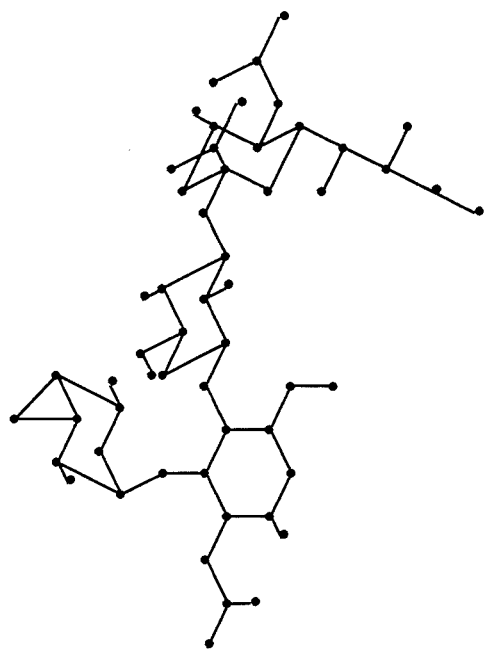

or an equivalent three-dimensional configuration with respect to its ability to bind to a selectin receptor.

4. The method of claim 3, wherein the pharmaceutical composition is administered by intravenous injection.

* * * * *